Figure 1:
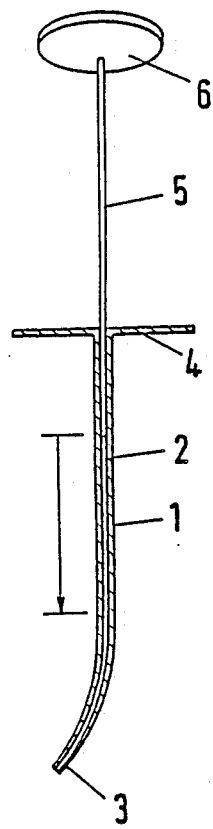

United States Patent [19]

Mühlbauer

[11] Patent Number: 4,952,209
[45] Date of Patent: * Aug. 28, 1990

[54] APPLICATOR SYRINGE FOR A DENTAL COMPOUND

[76] Inventor: Ernst Mühlbauer, Elbgaustrasse 248, 200 Hamburg 53, Fed. Rep. of Germany

[*] Notice: The portion of the term of this patent subsequent to Jan. 17, 2006 has been disclaimed.

[21] Appl. No.: 243,681

[22] Filed: Sep. 13, 1988

Related U.S. Application Data

[62] Division of Ser. No. 060,245, filed as PCT EP 86/00570 on Oct. 6, 1986, Published as WO 87/01929 on Apr. 9, 1987, Pat. No. 4,798,596.

[30] Foreign Application Priority Data

Oct. 7, 1985 [DE] Fed. Rep. of Germany ....... 8528512

[51] Int. Cl.$^5$ ................................................ A61M 3/00
[52] U.S. Cl. .................................. 604/218; 604/125; 222/386
[58] Field of Search ........ 604/207, 218, 219, 221–224, 604/230–232, 187, 124, 125; 433/90; 222/386

[56] References Cited

U.S. PATENT DOCUMENTS

| | | | |
|---|---|---|---|
| 2,724,385 | 11/1955 | Lockhart | 222/386 |
| 2,756,747 | 7/1956 | Axelrad | 604/219 |
| 2,860,635 | 11/1958 | Wilburn | 604/192 |
| 3,262,608 | 7/1966 | Macey | 604/218 |
| 3,577,850 | 5/1971 | Harris, Sr. | 222/386 |
| 3,809,298 | 5/1974 | Harris, Sr. et al. | 604/218 |
| 4,354,507 | 10/1982 | Raitto | 604/222 |
| 4,363,329 | 12/1982 | Raitto | 604/222 |
| 4,404,862 | 9/1983 | Harris, Sr. | 604/207 |
| 4,551,135 | 11/1985 | Gorman et al. | 604/218 |
| 4,617,918 | 10/1986 | Donohue et al. | 604/218 |
| 4,619,613 | 10/1986 | Dragan | 433/90 |
| 4,795,444 | 1/1989 | Hasegawa | 604/218 |
| 4,798,596 | 1/1989 | Mühlbauer | 604/218 |

FOREIGN PATENT DOCUMENTS 0248210 12/1987 European Pat. Off. .
2178019 11/1973 France .

Primary Examiner—Stephen C. Pellegrino
Assistant Examiner—Ralph Lewis
Attorney, Agent, or Firm—Chilton, Alix & Van Kirk

[57] ABSTRACT

Applicator syringe for a dental compound, with a syringe body (1) tapering into a thin discharge tube (3) and with a piston (5) displaceable in it, the applicator syringe being intended for once-only use. To avoid the need for special actuating tools, but make easy use possible, the effective cross-sectional surface is very small, in particular with a ratio of the useful stroke to the diameter of the syringe piston of at least approximately 10. So that the syringe can nevertheless be filled easily, the diameter of the cylindrical space in the rear portion of the latter is larger than the piston diameter. The syringe body (1) is first produced in a straight form and only thereafter is the discharge tube (3) bent.

5 Claims, 1 Drawing Sheet

U.S. Patent    Aug. 28, 1990    4,952,209

APPLICATOR SYRINGE FOR A DENTAL COMPOUND

This is a divisional of co-pending application Ser. No. 060,245 filed as PCT EP86/00570 on Oct. 6, 1986, published as WO87/01929 on Apr. 9, 1987, now U.S. Pat. No. 4,798,596.

The invention relates to a disposable applicator syringe for a dental compound, with a syringe body enclosing a cylindrical space and tapering into a thin discharge tube, and with a piston displaceable in the cylindrical space, in the state of rest the cylindrical space receiving the dental compound in a front portion and the piston in a rear portion.

It is customary for the dentist to pick up the separately mixed dental compound by means of a re-usable syringe which ends in a thin discharge tube and which contains a displaceable piston, in order to apply it by means of this syringe (GB-A-734,983 and US-A No. 4,184,490). This operation is complicated, especially since the syringe has to be cleaned and sterilized after each use.

Applicator syringes intended for once-only use and containing mercury and silver filings in separate chambers have therefore been developed, these components being mixed in the syringe itself (German Offenlegungsschrift No. 2,903,331); but these syringes have proved inappropriate, because there are difficulties in storing the mercury in them in a sealed manner and combining the components in exact quantities and mixing them completely.

The principle of the so-called disposable syringes was first adopted successfully in connection with photo-setting single-component filling compounds contained in syringe-like applicator cartridges. These comprise a syringe body with a cylinder displaceable in it, and a curved discharge tube. Since the force exerted to displace the piston in the syringe body is considerable, to use it a tool, for example of tong-like or pistol-like design, is required (German Auslegeschrift No. 2,045,509, German Offenlegungsschrift No. 2,110,463, German Offenlegungsschrift No. 3,235,232 and U.S. Pat. No. 4,391,590). The need for a special tool is a disadvantage, especially since it could come into contact with the patient's mouth and would therefore have to be sterilized. The production of these disposable syringes involves a high outlay, because the curved shape of the discharge tubes for forming the cavity require a multi-part core of complicated construction. Another disadvantage of this type of production is that the curved discharge tube can only be relatively short.

Applicator syringes for single-component filling compounds, which have a large holding capacity and which are intended for repeated use, are also known (German Offenlegungsschrift No. 3,212,187). These too should be sterilized before each use, but this is scarcely possible because they are in a filled state.

The object on which the invention is based is, therefore, to provide an inexpensive disposable applicator syringe which can be employed without a tool, but which nevertheless ensures hygienic use. Furthermore, the object on which the invention is based is to provide a simple process for producing such an applicator syringe with a curved discharge tube which can be of any length.

In the solution according to the invention, the syringe body and the piston designed as a rod are made thin, in particular with a ratio of the effective stroke to the diameter of the cylindrical space and the syringe piston of at least approximately 10, and the diameter of the piston is less than the diameter in the rear portion of the cylindrical space.

The invention, to provide an applicator syringe designed as a whole for once-only use, had to overcome two difficulties. One is that the force required to propel the piston must be so low that there is no need for a special tool. The other is that, because of the need for competitiveness in the field of small and simple applicator capsules, the outlay in terms of production must be kept very low, so that it is possible to compete with the applicator capsules mentioned above.

Because of the choice of an unusually small piston diameter which is appropriately no greater than approximately 10 or preferably 7 mm$^2$, the force required to expel the compound from a nozzle orifice of predetermined size is reduced considerably. Although the small piston diameter results in a considerable increase in the necessary stroke for a predetermined discharge volume of, for example, 100 mm$^3$, nevertheless, in contrast to a tool, a stroke of the order of, for example, 3 cm presents no problem for the human hand. As regards the outlay involved in the applicator syringe according to the invention, this depends, on the one hand, on the quality of the piston packing. In comparison with the known applicator capsules, to meet the same sealing requirements the cross-sectional tolerances in the syringe according to the invention can be substantially greater than in the known capsules because of the shorter peripheral length of the sealing zone. On the other hand, the production outlay depends on how complicated is the filling operation which, in the syringe according to the invention, is very simple.

Because the piston does not rest directly against the cylindrical wall in the rear portion of the cylindrical space in which it is located when the applicator syringe is in the state of rest ready for use, the piston can be pushed into the cylindrical space even after the compound has been introduced into the front portion of the cylindrical space, since the gas (air or inert gas) located between the compound and the piston can escape through the gap between the cylinder wall and the piston. If the piston has a sealing lip formed on it, the diameter of the latter is to be taken as the decisive piston diameter which should be somewhat less than the diameter of the cylindrical space in that rear part of the syringe body which is not filled with the compound and in which the piston will be located. As soon as the piston strikes the compound or is pressed against it, the pressure exerted on the sealing lip of the piston increases and presses a sealing lip against the cylinder wall, even if the relaxed diameter of the sealing lip when it strikes the compound is still somewhat less than that of the cylindrical space. For these and other reasons, it is not necessary for the piston diameter to be equal to the diameter of the cylindrical space exactly at the boundary between the front portion filled with the compound and the rear portion in which the piston is to be located.

Since the cylindrical space of the syringe body is long and thin, to produce the syringes according to the invention it is not possible to use the known production process, in which the syringe body and the curved discharge tube are produced in a single injection-moulding operation, since the long thin cylindrical space prevents the use of multi-part curved moulding cores. However, the long thin shape of the syringe according to the invention makes it possible to adopt a substantially simpler production process, in which the syringe body and the discharge tube are first produced axially in alignment with one another by the use of a single injection mould with only one uniform core and only thereafter is the discharge tube bent when the thermoplastic material is in the still hot or reheated state. This process cannot be used for the known applicator capsules, because in these the discharge tube is too thick in relation to its length. Thus, the syringe according to the invention is simple to produce because of its thin shape with a low ratio of the clear cross-sectional surface of the cylindrical space to that of the end of the discharge tube, this ratio advantageously being no greater than 5:1 and preferably 3:1.

Figure 2:
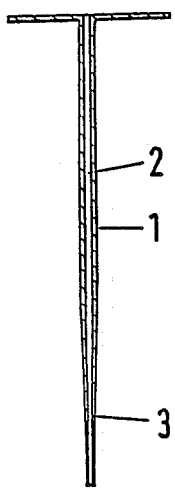
Figure 3:
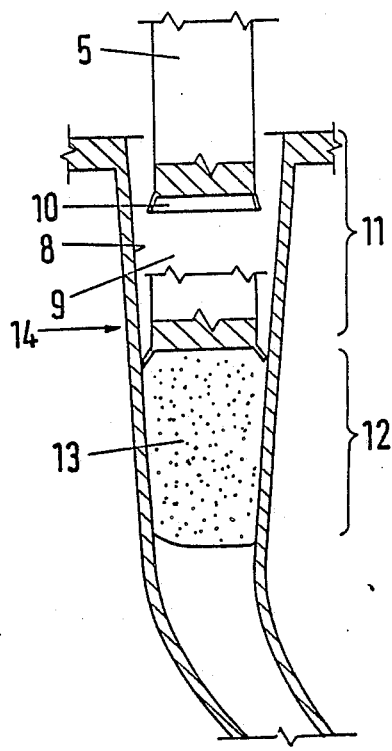

The invention is explained in detail below with reference to the drawing which illustrates an advantageous examplary embodiment. In the drawing:

FIG. 1 shows a longitudinal section through an applicator syringe according to the invention, FIG. 2 shows the syringe body after the first production step, and FIG. 3 shows a representation with a greatly enlarged diameter.

The applicator syringe consists of the syringe body (1) which encloses a cylindrical space (2) for receiving the viscous compound and at the end tapers integrally into the thin discharge tube (3) and which has a gripping flange (4), and of the rod-like piston (5) with the gripping plate (6). The piston (5) consists of a material resistant to bending, so that, despite its thinness, it does not bend under the propulsive forces. Suitable materials are polypropylene, polyethylene or polyamide, of sufficient elasticity for the syringe body and glass-fibre-reinforced plastic for the piston.

The discharge tube (3) can be equipped with a removable closing cap. To protect the compound to be stored in the syringe against harmful influences, it is also possible, instead, for the appliance to be welded into a film bag or packaged safely in another way.

The cross-sectional size of the piston (5) and of the cylindrical space (2) is appropriately between 1 and 7 mm$^2$.

The useful stroke of the piston (5) is the distance (7) over which it can be displaced between its position of rest ready for use and its completely pushed-in position.

In a syringe according to the invention which has proved appropriate in practice, the piston cross-section is 6 mm$^2$ and the useful stroke is approximately 25 mm.

The syringe body is produced, for example, by injection moulding in the shape shown in FIG. 2. The production mould can be simple, because only a single straight mould core is necessary for forming the interior of the syringe body including the interior of the discharge tube. Only thereafter is the discharge tube bent, and this presents no problem because the discharge tube is relatively thin even in its part adjacent to the cylindrical part of the syringe body, and its diameter does not change greatly over its length.

A suitable seal should be provided between the piston (5) and the wall (8) surrounding it. To ensure this, as is known, the piston can have a slight oversize exceeding the clear diameter of the cylindrical space (9) and the cylinder wall can be appropriately elastic, so that, in interaction with the piston periphery, it expands elastically and rests against the piston free of gaps. For this purpose, the piston can be thickened at its front end or have a sealing lip.

The preferred embodiment is described below with reference to FIG. 3 which shows the arrangement according to FIG. 1 over-enlarged in terms of diameter. According to this, the cylinder wall (8) is not exactly cylindrical, but slightly conical, so that it widens a little towards the end located on the same side as the piston. The piston (5), at its front end, carries an encircling sealing lip (10), the diameter of which is a little less than the clear diameter of the cylindrical space (9) in the rear portion (11) of the syringe body which remains empty, that is to say filled with gas, after the compound (13) has been introduced in the region (12). When the piston (5) is pushed into the syringe body after the compound has been introduced, the gas located between them can therefore be expelled through the gap between the wall (8) and the sealing lip (10), until the piston end rests against the compound (13), as indicated at (14) in FIG. 3, or has at least come very close to it. The dimensions of the piston and cylindrical space are such that, in this position, the sealing lip (10) approximately reaches the cylinder wall (8). But it does not matter if, even at this point, the diameter of the lip (10) is still somewhat less than that of the wall (8), because when the compound is reached the pressure prevailing in front of the piston increases to such an extent that the lip (10) is pressed outwards against the cylinder wall.

I claim:

1. A disposable applicator syringe for a dental compound, comprising:
   a tubular member made from an elastically yielding polymeric material having a rear entrance end portion, a smoothly curved front discharge end portion, an intermediate portion between the end portions, and a continuous, substantially cylindrical central channel extending from the entrance end portion to the discharge end portion through the intermediate portion, the channel at least in the intermediate portion having a smaller diameter than the channel in the entrance end portion and a clear cross sectional area no greater than about 10 mm$^2$, the intermediate portion being adapted for receiving a predetermined quantity of viscous dental compound to be discharged through said discharge end portion, wherein the cross sectional area of the channel through the intermediate portion and discharge end portion reduces with substantially smooth continuity by no greater than a ratio of about three; and
   a piston in the form of an elongated rod having a head portion including annular lip means defining the diameter of the head, which is less than the channel diameter in the entrance end portion, the piston adapted to be manually advanced through the entrance end portion and the intermediate portion into contact with the dental compound such that the lip means are pressed radially outwardly by the compound into sealing engagement with the wall of the channel, the head of the piston having a useful stroke in the intermediate portion while advancing the compound through the channel, said useful stroke being equal to at least about ten times the diameter of the channel in the intermediate portion.

2. Applicator syringe according to claim 1, characterized in that the diameter of the channel through the entire intermediate portion is less than the diameter of the piston head.

3. The applicator syringe according to claim 1, characterized in that the tubular member and the piston are each equipped with gripping parts and the effective cross-sectional surface of the piston head is no greater than approximately 10 mm$^2$.

4. The applicator syringe according to claim 1, characterized in that the effective cross-sectional surface of the piston head is less than approximately 7 mm$^2$.

5. The applicator syringe according to claim 1, characterized in that the cross-sectional area of the channel through the intermediate portion and the discharge end portion reduces by a ratio no greater than approximately 5:2.

* * * * *